United States Patent
Rawls et al.

(10) Patent No.: US 10,322,069 B2
(45) Date of Patent: Jun. 18, 2019

(54) RESTORATIVE RESIN COMPOSITIONS AND METHODS OF USE

(71) Applicant: The Board of Regents of the University of Texas System, Austin, TX (US)

(72) Inventors: H. Ralph Rawls, San Antonio, TX (US); Allen D. Johnston, San Diego, CA (US); Barry K. Norling, San Antonio, TX (US); Kyumin Whang, Helotes, TX (US)

(73) Assignee: The Board of Regents of the University of Texas System, Austin, TX (US)

( * ) Notice: Subject to any disclaimer, the term of this patent is extended or adjusted under 35 U.S.C. 154(b) by 0 days.

(21) Appl. No.: 15/302,320

(22) PCT Filed: Apr. 7, 2015

(86) PCT No.: PCT/US2015/024772
§ 371 (c)(1),
(2) Date: Oct. 6, 2016

(87) PCT Pub. No.: WO2015/157329
PCT Pub. Date: Oct. 15, 2015

(65) Prior Publication Data
US 2017/0020789 A1    Jan. 26, 2017

Related U.S. Application Data

(60) Provisional application No. 61/976,242, filed on Apr. 7, 2014.

(51) Int. Cl.
*A61C 13/23*   (2006.01)
*A61K 6/00*   (2006.01)
*A61K 6/083*   (2006.01)

(52) U.S. Cl.
CPC ............ *A61K 6/005* (2013.01); *A61K 6/0052* (2013.01); *A61K 6/0073* (2013.01); *A61K 6/0091* (2013.01); *A61K 6/083* (2013.01)

(58) Field of Classification Search
CPC .... A61K 6/0005; A61K 6/083; A61K 6/0091; A61K 6/0052; A61K 6/0073
See application file for complete search history.

(56) References Cited

U.S. PATENT DOCUMENTS

| | | | | |
|---|---|---|---|---|
| 4,758,615 A * | 7/1988 | Engel | ................. | C08G 18/6415 524/198 |
| 8,932,632 B2 * | 1/2015 | Yadav | ..................... | C03C 27/10 156/284 |

(Continued)

FOREIGN PATENT DOCUMENTS

EP    0678533 A2    10/1995

*Primary Examiner* — Jessica M Roswell
(74) *Attorney, Agent, or Firm* — Winstead PC

(57) ABSTRACT

Embodiments of the invention are directed to dental compositions comprising: (1) at least one cationically reactive compound; (2) at least one cationic photoinitiator; (3) at least one compound which is: an organic monomer, oligomer or polymer, said compound comprising at least one reactive oxirane, oxetane, or alkenyl ether, (4) at least one compound which is: an organic monomer, oligomer or polymer, said compound comprising at least one reactive acrylate that is capable of forming an interpenetrating network; (5) at least one free radical initiator; and (6) at least one compound which is: an organic monomer, oligomer or polymer, said compound comprising at least one reactive acrylate or methacrylate and at least one oxirane, oxetane, or alkenyl ether.

10 Claims, 10 Drawing Sheets

(56) References Cited

U.S. PATENT DOCUMENTS

| | | | |
|---|---|---|---|
| 2004/0115363 A1* | 6/2004 | Desai | C09D 163/00 427/508 |
| 2006/0216500 A1 | 9/2006 | Klun et al. | |
| 2007/0015845 A1* | 1/2007 | Jin | A61K 6/0023 523/113 |
| 2011/0049429 A1* | 3/2011 | Webster | C08G 59/226 252/392 |
| 2011/0200973 A1 | 8/2011 | Rawls et al. | |

\* cited by examiner

RESTORATIVE RESIN COMPOSITIONS AND METHODS OF USE

CROSS-REFERENCES TO RELATED APPLICATIONS

This Application claims the benefit under 35 U.S.C. § 119(e) of U.S. Provisional Patent Application No. 61/976,242 filed Apr. 7, 2014 which is incorporated herein by reference in its entirety as if fully set forth herein.

STATEMENT REGARDING FEDERALLY SPONSORED RESEARCH OR DEVELOPMENT

This invention was made with government support under Contract No. 1U01DE023778-01 awarded by the National Institute of Dental and Craniofacial Research (National Institutes of Health). The government has certain rights in the invention.

BACKGROUND OF THE INVENTION

Dental resin composite restorations break down due to recurrent caries and restoration defects, such that approximately half or more fail within about 10 years. In the case of bisphenol-A glycidyl dimethacrylate (Bis-GMA)-based resins, their breakdown product can be bisphenol-A, a known health hazard. Furthermore, in Bis-GMA and urethane dimethacrylate (UDMA) based resins, leaching of both unreacted monomers and degradation products stimulate oral bacteria to produce even more acid byproducts and esterases, all of which could lead to further ongoing degradation and possibly secondary caries in the nearby tooth structure. In order to extend the clinical lifetime of dental resin based composites, their buildup of shrinkage stress, the susceptibility of their ester groups to hydrolysis and esterase degradation, and the formation of marginal gaps between the resin and tooth structure must be overcome.

Thus, the inventors have developed a hydrophobic, hydrolysis and esterase-resistant, dental restorative system based on Oxirane/Acrylate Systems (OASys, pronounced "Oasis"). The OASys contains the following: monomers with methacrylate endgroups that are replaced with a combination of monomers containing oxirane (a.k.a. epoxy) or acrylate endgroups that form an interpenetrating polymer network (IPN), and a tri-functional bonding agent with oxirane, acrylate and phosphate functionality that is capable of bonding to both networks in the IPN as well as the tooth structure. Alternatively, a bonding agent with diepoxide or diacrylate and phosphate functional endgroups can also be used.

Preferably, both types of monomers in the IPN are multifunctional, e.g., dioxirane and diacrylates, based on urethane monomers because urethane linkages are more resistant to hydrolysis and esterase degradation than ester linkages, and may also be fluorinated to further increase hydrophobicity and decrease hydrolysis and esterase degradation. Such components polymerize separately, but simultaneously, to form independent networks that are each highly converted and crosslinked, but physically intertwined. Such IPNs offer synergistic advantages that provide superior performance as restorative dental composites via the following mechanisms.

These IPN resins can provide higher-levels of mechanical and physical properties as compared to methacrylate-based resins, such as increased toughness. They also have lower residual cure-shrinkage stresses since epoxy monomers polymerize via a ring opening mechanism reducing cure shrinkage, and their polymerization is substantially slower allowing more time for stress relaxation. The acrylate network cures quickly and allows the dentist to work with a hardened structure while the oxirane cures over a longer period of time. Acrylic and oxirane functionality are also significantly more resistant to hydrolytic and enzymatic degradation than methacrylic functionality, which increases longevity. Furthermore, methacrylate polymerization is inhibited by oxygen, while acrylate polymerization is faster and less susceptible to oxygen inhibition and oxiranes are not susceptible to oxygen inhibition. Therefore, the surface layer of an OASys resin will suffer little from oxygen inhibition and thus have a higher degree of conversion and crosslinking, making it more resistant to water imbibition and subsequent hydrolysis.

Such oxirane/acrylate hybrid resin systems and the properties of IPNs have been described in the literature in different forms. However, these systems are not currently used as dental restoratives. Reasons include the toxicity of the amines typically used with epoxy resins, the toxicity of cationic byproducts of epoxy polymerization, and the lack of an adequate dental bonding system for such a hybrid resin system. The issue of cationic byproduct toxicity has largely been addressed with the use of dual-mode light-cure initiator systems that use polyols to quench the cationic byproducts. Another reason is that there does not exist an adequate dental bonding system that is capable of attaching to both parts of the IPN as well as the tooth structure. The use of a conventional bonding agent to attach the tooth structure to only the acrylate or methacrylate network may actually weaken the restorative since the other network is not attached at all.

The invention includes a series of bonding agents. One bonding agent contains a phosphate group plus both oxirane and acrylate functionalities. FIG. 16 shows an example of 4-Phospho-NPG GA oxirane (4POA). The phosphate group forms a bond to the hard tooth tissue (enamel and dentin), and both oxirane and acrylate functional groups bind, respectively, to the epoxy and acrylate polymer networks, and thereby attach the OASys restorative composite at the composite/hard tissue interface. Alternatively, a mixture of a diepoxide bonding agent with a phosphate endgroup (FIG. 18) or a diacrylate bonding agent with a phosphate endgroup (FIG. 19) can be used. Additionally, these bonding systems are one-step (primer-less), "smart," antimicrobial bonding resins with in situ-generated silver nanoparticles (AgNPs) that is capable of releasing antimicrobial $Ag^+$ ions in the event of marginal gap formation to prevent secondary caries. These bonding agents can further increase bond strength and prevent marginal gap formation.

SUMMARY OF THE INVENTION

Embodiments of the invention are directed to dental compositions comprising: (1) at least one cationically reactive compound; (2) at least one cationic photoinitiator; (3) at least one compound which is: an organic monomer, oligomer or polymer, said compound comprising at least one reactive oxirane, oxetane, or alkenyl ether; (4) at least one compound which is: an organic monomer, oligomer or polymer, said compound comprising at least one reactive acrylate; (5) at least one free radical initiator and (6) at least one compound which is: an organic monomer, oligomer or polymer, said compound comprising at least one reactive acrylate or methacrylate and at least one oxirane, oxetane, or alkenyl ether. A further embodiment consists of fluorinated oxirane and/or acrylate monomers. Another embodiment consists of an amine capable of initiating the oxirane cure. A further embodiment consists of a hybrid monomer with at least one acrylate group and one oxirane group. Another embodiment consists of a series of bonding agents to both attach an OASys restorative resin to tooth structure, and to also carry an antimicrobial/anticaries component. The bonding agent comprises at least one phosphate group plus at least one each oxirane and acrylate functionalities or alternatively it can be a mixture of two bonding agents, one with at least one phosphate group plus at least two oxirane functionalities and the other with at least one phosphate group plus at least two acrylic functionalities.

DETAILED DESCRIPTION OF EXEMPLARY EMBODIMENTS

Figure 16:
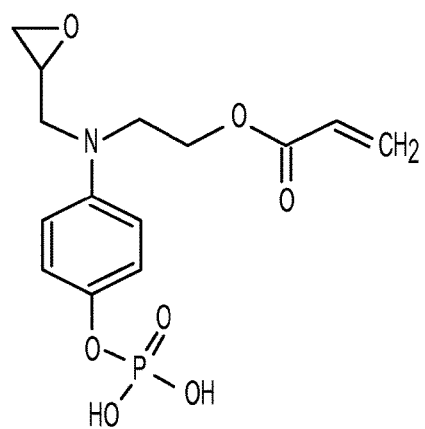
FIG. 16 shows the structure for ethyl-2-((oxirane-2-ylmethyl) (4-phosphonooxy) phenyl) amino)acrylate (4POA)
Figure 18:
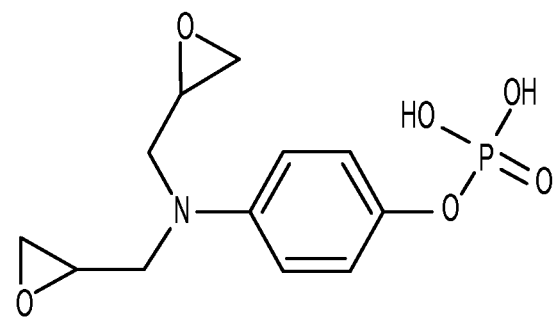
FIG. 18 shows an example of a diepoxide bonding agent.
Figure 19:
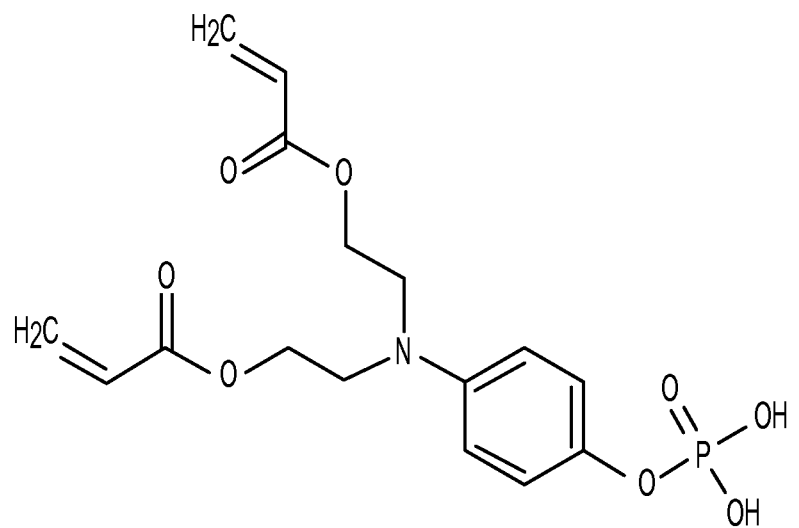
FIG. 19 shows an example of a diacrylate bonding agent.
Figure 20:
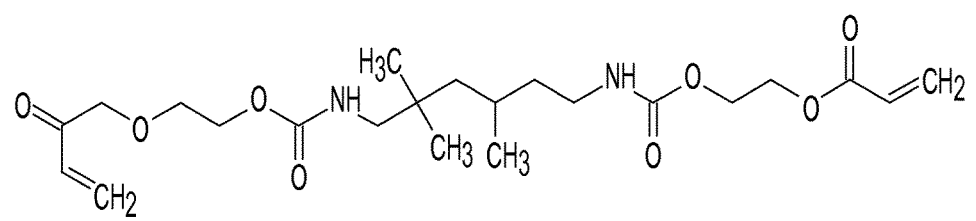
FIG. 20 shows the structure of urethane diacrylate (UDA)
Figure 21:
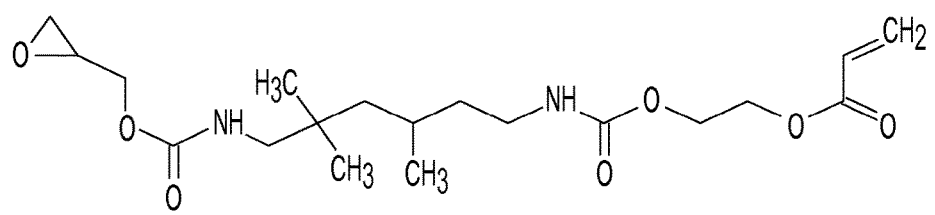
FIG. 21 shows the structure of urethane acrylate oxirane (UAO).

To achieve the above goals, the methacrylate-based, restorative, monomer system has been replaced with an Oxirane/Acrylate System. A preferred version of this system is comprised of the monomers shown in FIGS. 1-5, 7, 8, 20, 21: a urethane dioxirane (UDO), a high molecular weight urethane dioxirane with hydroquinone in the center and an isophorone group on both sides (DIUDO), a diacrylate analog to DIUDO (DIUDA), a DIUDO with 4 fluorines on the hydroquinone (4FDIUDO), a diacrylate analog 4FDIUDA, EPALLOY 5000, a diacrylate analog to UDO (UDA), and a hybrid urethane acrylate oxirane (UAO). This will be used in conjunction with a one-step (primer-less), "smart" antibacterial bonding system such as the adhesive monomer 4POA (FIG. 16) that has an oxirane, an acrylate, and a phosphate group, and in situ-generated AgNPs. Alternatively, diepoxide and diacrylate bonding agents (FIGS. 18 & 19) can be used. These bonding resins are developed to specifically take advantage of the Oxirane/Acrylate IPN to form a stronger bond by having the ability to bond to both the oxirane and the acrylate groups in the IPN, as well as to the calcium in the dentin via the phosphate group, and allow the oxirane/acrylate monomer system to be used in a dental application.

Thus, the OASys provides the following features: 1) Urethane dioxiranes contain no ester groups and are thus not susceptible to hydrolysis or esterase degradation. 2) Dioxiranes are more hydrophobic than dimethacrylates so water uptake and consequent hydrolysis in the oral environment will be reduced. 3) Fluorination renders these dioxiranes and diacrylates even more hydrophobic, and enhances this protection. 4) Acrylic groups will compensate for the inherently slow oxirane curing rate by allowing for a quick initial cure of the acrylate to form a solid structure, followed by a slower final oxirane cure and enhance stress relaxation. 5) Oxirane groups open and expand during polymerization further offsetting shrinkage and shrinkage stress. 6) The addition of the diacrylate analogs DIUDA and 4FDIUDA to form an interpenetrating network (IPN) with the dioxirane monomers (OASys) can increase toughness and resin longevity. 7) Oxiranes are not susceptible to oxygen inhibition so the surface layer would have a higher degree of conversion and crosslinking; further reducing water uptake, hydrolysis, and esterase degradation. 8) The tri-functional bonding agent allows bonding to both the acrylate and oxirane networks as well as the tooth structure to not just prevent the decrease in bond strength if it were only to bond to one of the networks, but to actually increase bond strength as compared to a methacrylate-based resin system. 9) Alternatively, diepoxide and diacrylate bonding agents (FIGS. 18 and 19) can be used. 10) "Smart" antimicrobial effect via release of Ag$^+$ ions should a marginal gap form.

Figure 6:
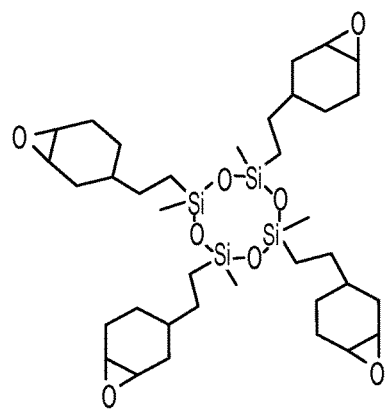
FIG. 6 shows the structure of silorane in accordance with an embodiment of the invention.
Figure 7:
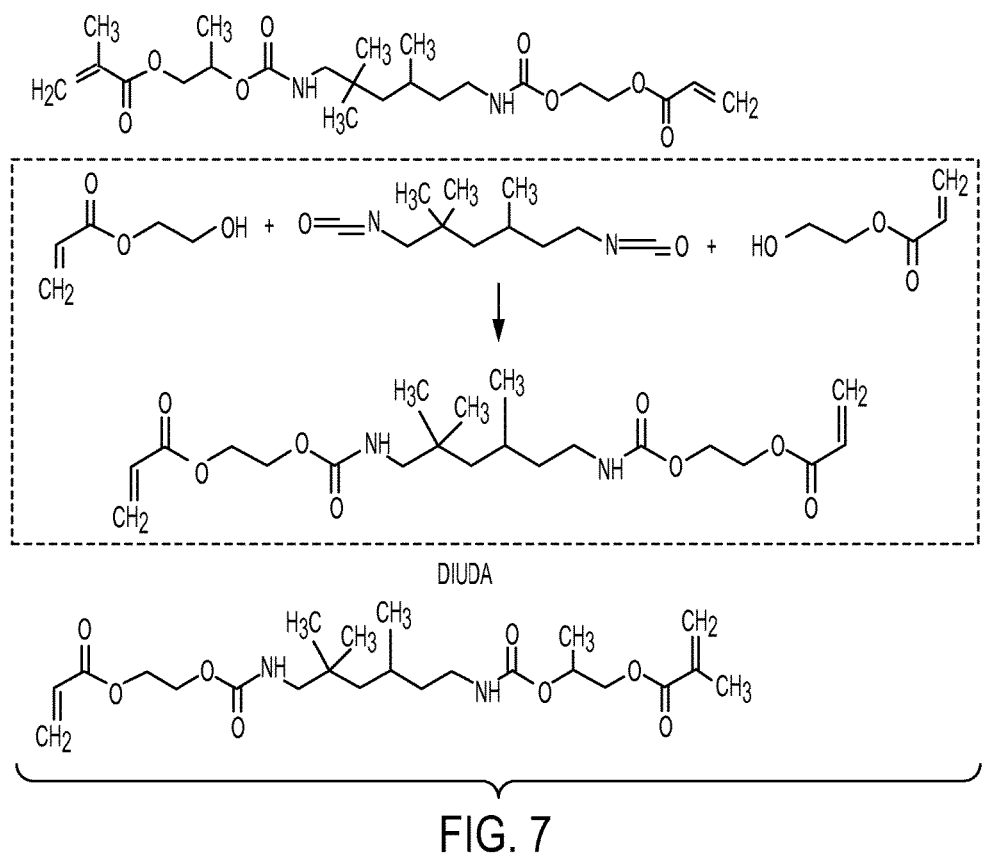
FIG. 7 shows a schematic diagram of the synthesis of diisophorone urethane diacrylate in accordance with an embodiment of the invention.
Figure 8:
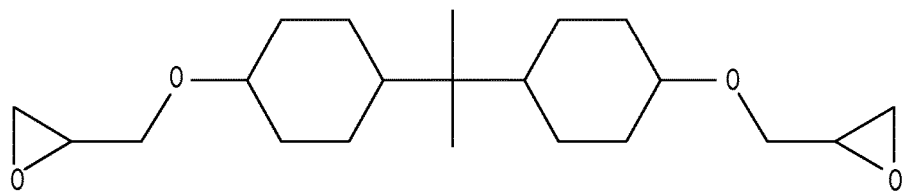
FIG. 8 shows the structure of EPALLOY 5000.

Further, vinyl ethers (R(O—CH═CH2)n), oxetanes (aliphatic 4-membered either ring compounds) and siloranes (FIG. 6, compounds with both oxirane and siloxane groups, as shown here) may also be used in place of or together with oxirane/epoxy compounds.

An embodiment of the claimed invention is directed to a dental composition comprising: (1) at least one cationically reactive compound; (2) at least one cationic photoinitiator; (3) at least one compound which is: an organic monomer, oligomer or polymer, said compound comprising at least one reactive oxirane, oxetane, or alkenyl ether;

(4) at least one compound which is: an organic monomer, oligomer or polymer, said compound comprising at least one reactive acrylate; and (5) at least one free radical photoinitiator; and (6) at least one compound which is: an organic monomer, oligomer or polymer, said compound comprising at least one reactive acrylate or methacrylate and at least one oxirane, oxetane, or alkenyl ether.

In certain embodiments, the invention includes an amine capable of initiating the oxirane cure.

In certain embodiments, the invention consists of a hybrid monomer with at least one acrylate group and one oxirane group.

In certain embodiments, the invention includes a bonding agent that is capable of binding to the dental compositions. In a further embodiment, the bonding agent attaches to a cationic/free-radical initiated interpenetrating polymer network restorative resin and to a tooth structure. The bonding agent comprises at least one phosphate functionality plus both a cationically reactive compound and an ethylenic compound, said compounds comprising at least one each having oxirane and acrylate functionalities.

In certain embodiments, the cationic photoinitiator is an iodonium salt.

In some embodiments of claimed invention, the monomer is a urethane dioxirane (UDO), a high molecular weight urethane dioxirane with hydroquinone in the center and an isophorone group on both sides (DIUDO), a diacrylate analog to DIUDO (DIUDA), a DIUDO with 4 fluorines on the hydroquinone (4FDIUDO), a diacrylate analog 4FDIUDA, EPALLOY 5000, a diacrylate analog to UDO (UDA), and a hybrid urethane acrylate oxirane (UAO). In certain embodiments, the composition further comprises acrylate monomers in an interpenetrating polymer network with oxirane monomers. The monomer blends of acrylate to oxirane in compositions of the invention range from 0:100, 25:75, 50:50, 75:25 and 100:0 wt %.

In certain embodiments of the invention, the acrylate monomer that is used in the compositions is a urethane acrylate. In certain compositions, the urethane acrylate is fluorinated.

In certain embodiments of the invention, a tri-functional bonding agent with an oxirane, acrylate and phosphate functionality is used.

In certain embodiments of the invention, a mixture of one tri-functional bonding agent with two oxirane functionalities and a phosphate functionality and one tri-functional bonding agent with two acrylic functionalities and a phosphate functionality is used.

In certain embodiments of the invention, the tri-functional bonding agents are used with in situ-generated silver nanoparticles (AgNPs). Previously, a method to generate AgNPs in situ in dental resins using the natural curing process of acrylic resins was developed. This technology has been incorporated in an orthodontic band cement, an endodontic filler, and denture acrylic, and investigated to determine the antimicrobial properties it imparts as described below. It is currently being tested in a pit and fissure sealant, a bonding agent, and an orthopedic bone cement.

In certain embodiments of the invention, amines are used in the curing process. The amines may be aliphatic, alicyclic or aromatic amines. The amines can also be diamines and triamines. Examples of amines used in the curing process include, but are not limited to, diethylenetriamine (DTA), triethylenetetramine (TTA), N-aminoethylpiperazine (N-AEP), isophoronediamine (IPDA) metaphenylenediamine (MPDA), hexamethylene diamine (HMDA), and ethyl-4-dimethyl-aminobenzoate (EDMAB).

WORKING EXAMPLES

Monomer Syntheses:
Urethane Oxirane Synthesis
UDO synthesis: The UDO is the neat addition product of 2 equivalents of glycidol and 2,2,4 trimethyl hexane diisocyanate (TMHDI). The synthesis is accomplished in a jacketed reactor equipped with an overhead mechanical stirrer and circulating heater set at 40° C. To the measured TMHDI and a small amount of tin catalyst, glycidol is added in small doses to minimize the temperature increase due to the exothermic reaction. The reaction can be monitored for completion by infrared spectroscopy of the isocyanate absorption near 2100 $cm^{-1}$. The disappearance of the peak indicates that the reaction is complete.

DIUDO synthesis is similar. It results from the sequential addition of hydroquinone (HQ) and glycidol to isophorone diisocyanate (IPDI). To the measured IPDI and a small amount of tin catalyst, HQ is added in small doses to minimize the temperature increase due to the exothermic reaction. When the correct amount of HQ has reacted with the IPDI, the addition of glycidol commences. Again, the doses of glycidol are measured to ensure the temperature increases are not excessive. The reaction is monitored for completion by infrared spectroscopy of the isocyanate absorption near 2100 $cm^{-1}$.

4FDIUDO synthesis is similar with the tetrafluorohydroquinone replacing the HQ. The temperature profile of this addition is different from the HQ reaction due to the fluoride groups on the ring.

Urethane Acrylate Synthesis:
DIUDA Synthesis
HQ addition to IPDI is accomplished in the presence of some BHT inhibitor (500 ppm based on the final product mass). 2-hydroxylethyl acrylate (HEA) is then be added in small doses to consume almost all of the remaining isocyanate groups. To ensure that the monomer does not contain unreacted HEA, the last isocyanate groups will be consumed by the addition of ethanol. In molar terms, if the reaction contains 2 moles of IPDI, then 1 mole of HQ is added first and allowed to react. The initial reaction is followed by the addition of 0.97 moles of HEA in small doses. When the HEA has been consumed, the reaction is finished with 0.03 moles of ethanol.

The design for the synthesis of urethane acrylates is the standard design but with a wrinkle added at the end. Urethanes are made from isocyanates and alcohols. The urethane diacrylates described above are made from 2,2,4 trimethylhexane-1,6-diisocyante (TMHDI) and 2-hydroxyethy acrylate (2-HEA) as below. In order to assure consumption of the isocyanate group, the alcohol is added in slight excess so the finished resin contains usually less than 1% (w/w) residual alcohol. The residual 2-HEA presents a challenge to the biological environment where this monomer is to be used. In order to avoid this issue, the residual 2-HEA is replaced by 2-hydroxypropyl methacrylate (HPMA). Even though the reactivity of 2-HEA with the TMHDI is much greater than with HPMA based on the stereochemical requirements of a primary versus secondary alcohol site, this factor is no guarantee of nondetectable residual 2-HEA in the product. The process is to modify the addition order of the alcohols to the isocyanate. For example, if the reaction is to be run on a one mole scale of diisocyanate, then two moles of alcohol are required to consume the isocyanate. If 1.99 moles of 2-HEA are added to the reaction, monitoring the temperature of the reaction would indicate when all of the alcohol had been consumed. The exotherm indicating a reaction occurrence would have peaked and reaction temperature would be dropping. An Infrared (IR) scan at that point would indicate residual isocyanate presence and zero alcohol. At this point 0.01 moles of HPMA and 0.25-1.00% (w/w) excess HPMA are added to complete the synthesis. The reaction temperature will rise slightly to accommodate the heat of reaction between the residual isocyanate groups and the HPMA but this would be a more sluggish reaction than the 2-HEA addition reaction exotherm.

The IR determines when the reaction is complete by the absence of an isocyanate peak in the scan. The product mixture would include 0.01 moles of the mixed acrylate/methacrylate species.

The reactivity of the acrylate group towards free radical polymerization is greater than the methacrylate and would ensure at least one connection with the polymer matrix even if the methacrylate group does not react.

This timing modification in alcohol addition is applicable to the synthesis of all of the urethane acrylates.

4FDIUDA synthesis is accomplished in the same manner as that for DIDUO using tetrafluorohydroquinone.

Bonding Agent Synthesis:
Synthesis of 4POA

Figure 17:
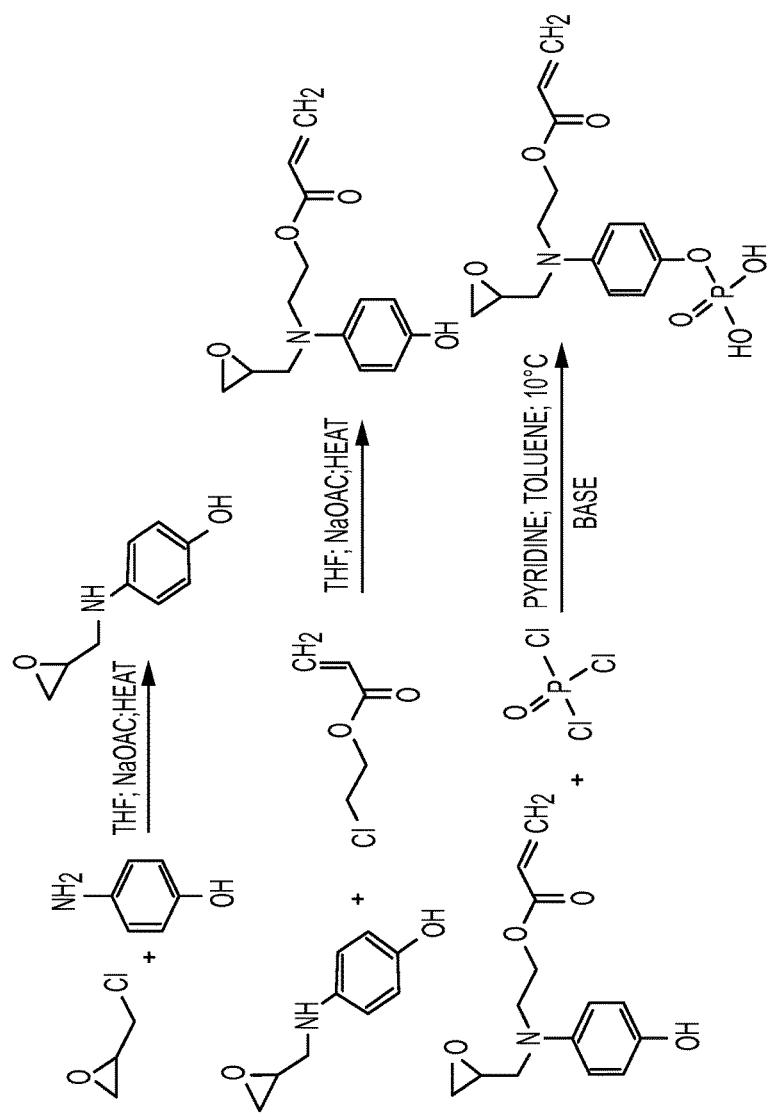
FIG. 17 shows the synthesis of the 4POA bonding agent having a phosphate, an acrylate and an oxirane functionality.

The synthesis of the 4POA molecule is accomplished in three steps (FIG. 17). 4-hydroxyaniline is alkylated with 1 molar equivalent of epichlorohydrin in dry tetrahydrofuran (THF) in the presence of sodium acetate to absorb the hydrochloric acid released during reaction. The secondary amine product is then isolated. It is then again alkylated by 2-chloroethyl acrylate in THF with the presence of sodium acetate to absorb the hydrochloric acid released during the reaction. Finally, the phenolic hydroxyl group is converted to a phosphate group by the addition of $POCl_3$ in toluene with pyridine to absorb the hydrochloric acid released during the reaction. Filtration removes the pyridinium hydrochloride salt. Exposure to basic water converts the chlorophosphate species to a phosphate group.

Oxirane/acrylic interpenetrating network (IPN) thin resin coatings resistant to air inhibition: When cured in thin layers in contact with air, dimethacrylate monomer polymerization is inhibited by oxygen. Thus, with the objective of developing thin dental veneers that mask tooth discoloration, two formulations were tested (Table 1).

TABLE 1

Oxirane/Acrylic IPN Thin-Layer Coating Formulations

| Component Function | Formulation Component | Masking (wt. %) | Translucent (wt. %) |
|---|---|---|---|
| Acrylic co-monomers | DIPENTA | 10 | 20 |
|  | EGDMA | 10 | 10 |
| Oxirane/Oxirane co-monomers | GE-22 | 43 | 46 |
|  | Ethylene glycol | 4 | 5 |
| Reinforcing fillers | M30K glass bubbles | 6 | 6 |
|  | Nano Alumina | 6 | 6 |
|  | Titanium dioxide, $TiO_2$ | 14 | 0 |
| Dual Mode Initiator components | OPPI | 4 | 4 |
|  | Camphorquinone | 2 | 2 |
|  | DMAEMA | 1 | 1 |

Each consisted of a blend of both acrylic and oxirane monomers, respectively: dipenta erythritol hexa-acrylate (DIPENTA, Aldrich) plus ethylene glycol dimethacrylate (EGDMA), and 1,4 cyclohexane-dimethanol diglycidyl ether (GE-22, CVC Thermoset Specialties) plus ethylene glycol. The first formulation was designed to mask tooth discolorations, while the other was designed to have a natural, translucent tooth-like appearance. A dual-mode photoinitiator system (camphorquinone/[4-(Octyloxy) phenyl] Phenyl Iodonium hexafluoroantimonate; CQ/OPPI) was used to photocure the oxirane/acrylic formulations. Both formulations were found to form ~40 micron thin layers with a high level of scratch resistance when photo-cured with a dental blue-light lamp (Optilux 501™) while in contact with ambient air. A control based on the dimethacrylate resin Bis-GMA/TEGDMA would not photocure (solidify) in the presence of ambient $O_2$. FTIR analysis used to determine monomer-to-polymer conversion showed the disappearance of the C=C acrylate peak at ~1637 $cm^{-1}$ and the oxirane ring peak at ~789 $cm^{-1}$ after 40 seconds of light exposure. The acrylate peak disappeared almost completely, while the oxirane peak was reduced only slightly. However, after 24 h dark storage, the oxirane peak was almost undetectable. Thus the acrylic monomers reacted immediately, while the oxirane monomers reacted slowly but continued to near completion after light exposure was discontinued. These results indicate that an oxirane/acrylate IPN system (OASys) potentially could have: 1) a higher degree of conversion at the surface of a dental restorative due to lack of significant $O_2$-inhibition and thus be more wear-resistant for increased clinical longevity, and 2) reduced shrinkage stress with the acrylate providing an immediate solid restoration and the slower-curing oxirane providing stress relaxation, and hence decreased potential for marginal breakdown and enhanced clinical longevity.

Figure 9:
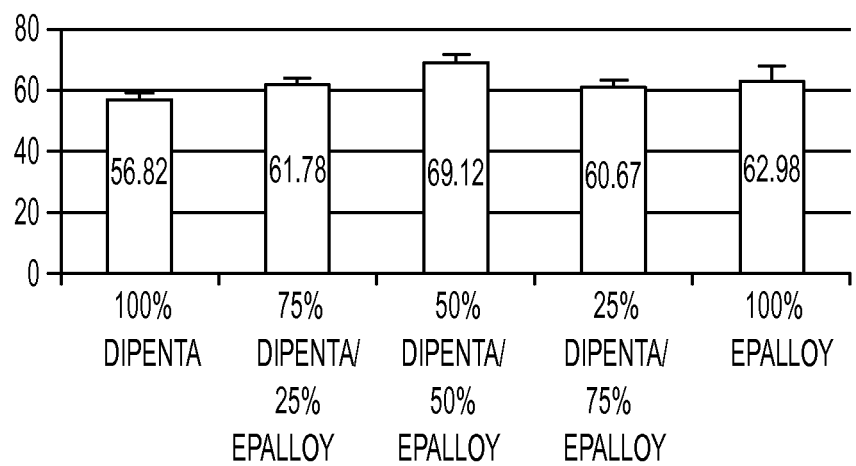
FIG. 9 shows contact angle measurements of an OASys resin immediately after photocure in accordance with an embodiment of the invention.

Oxirane/acrylic IPN bulk-cured resins: To assess the effect of the OASys on mechanical properties and potential resistance to the oral environment, model oxirane/acrylic blends were formulated using different combinations of DIPENTA alone as the acrylate, and together with a diepoxide/diol blend as the oxirane component. The oxirane component consisted of 89 wt % of the commercially available p-cycloaliphatic diepoxide, EPALLOY 5000 (CVC Thermoset Specialties, FIG. 9) with 11 wt % of an oligomeric diol, polyTHF-250 (BASF Corp.). These blends were cured using the CQ/OPPI (2 wt %/4 wt %) initiator in 2 mm-thick specimens. The monomer blends used were 0:100, 25:75, 50:50, 75:25 & 100:0 wt % ratios of DIPENTA:EPALLOY (in this context "EPALLOY" signifies EPALLOY 5000 89%/polyTHF-250 11%). These samples were tested for wettability using contact angle measurements, degree of cure using Rockwell$_{15T}$ hardness measurements, mechanical properties in 3-point bending, water uptake, and degradation using mass loss after storage for two days in water, 0.1M NaOH solution (pH 11), and 0.1M ascorbic acid solution (pH 2.5). Rockwell$_{15T}$ hardness was measured immediately after light curing and after 24 hours of water storage to assess the degree of cure likely to be attributable to the acrylate component versus the cure likely to be due to the oxirane component, respectively. After two days of storage in water, acid, or base followed by three days of desiccated vacuum drying, degree of degradation was assessed using mass loss.

Contact angle measurements immediately after photocure (FIG. 9) show that, as expected, 100% DIPENTA has significantly (p<0.05) lower contact angle than all groups.

While it is expected that the contact angle will increase with increasing amounts of EPALLOY, results were surprising in that the 50:50 DIPENTA:EPALLOY group is significantly more hydrophobic than all groups, even more than the 100% EPALLOY group. The significant increase in hydrophobicity of the 50:50 group demonstrates the advantage of having an IPN, as it potentially can reduce water sorption and subsequent hydrolysis—possibly via decreased $H_2O$ diffusion.

Figure 10:
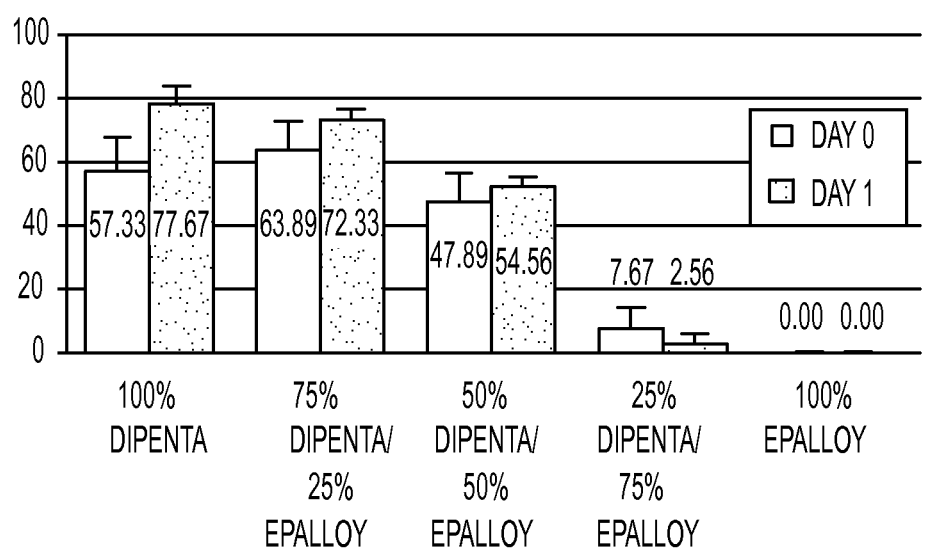
FIG. 10 shows Rockwell$_{15T}$ hardness results of an OASys resin in accordance with an embodiment of the invention.

Rockwell$_{15T}$ hardness results (FIG. 10) show that oxirane alone is difficult to photocure, and, as the acrylate portion increases, hardness and degree of cure increase, with the 75:25 DIPENTA:EPALLOY group having similar hardness to that of 100% DIPENTA. It is notable that there was a significant amount of dark cure (24 hr) in 100% DIPENTA as well as 75:25 DIPENTA:EPALLOY. These results show the need for including an acrylate to compensate for the slow and inefficient photocuring of the oxirane, as well as the need to further investigate and optimize the OASys curing process.

Figure 11:
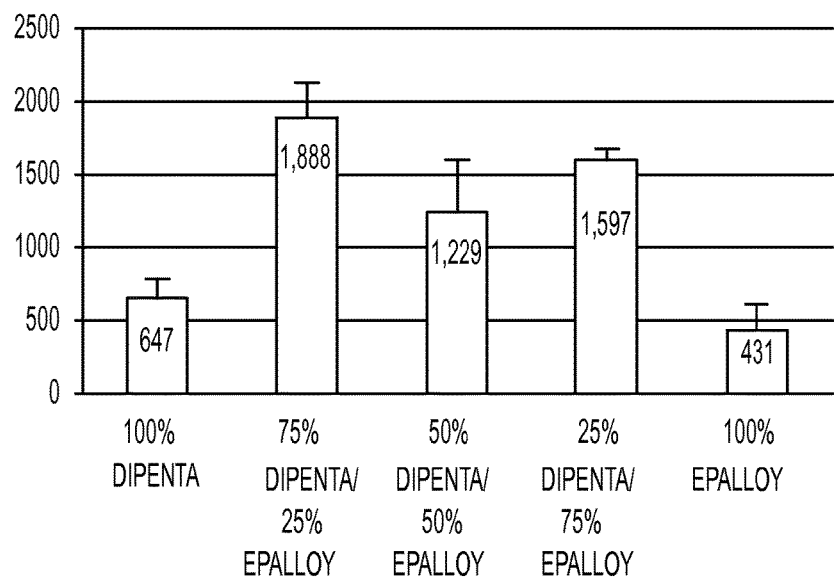
FIGS. 11-13 show three-point bending results of resins in accordance with embodiments of the invention.
Figure 12:
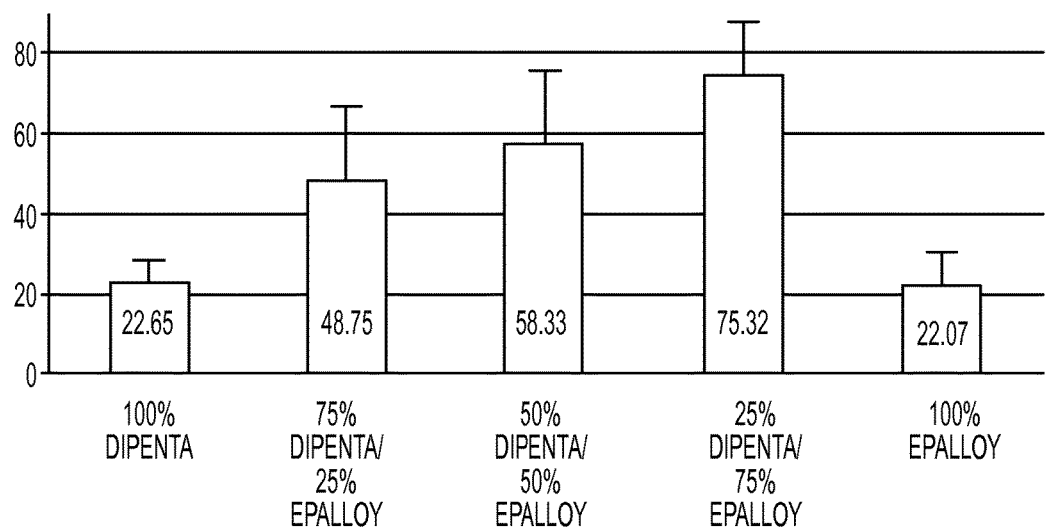
Figure 13:
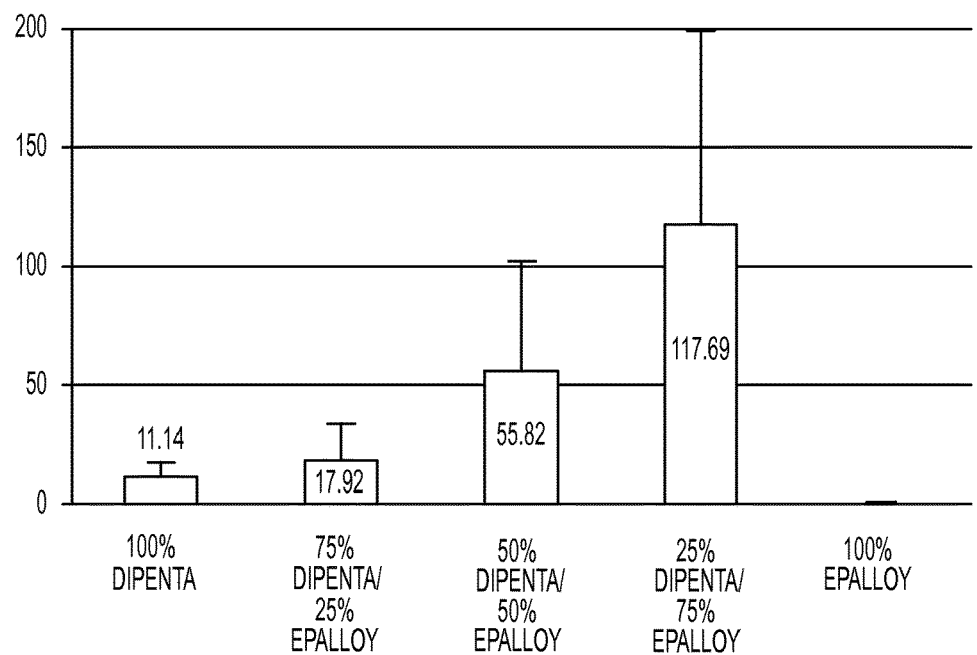

Three-point bending results (FIGS. 11-13) show that both the 100% acrylate and 100% oxirane had very low moduli, ultimate transverse strength (UTS), and energy to break (EB), and that the oxirane/acrylate combination significantly improved these properties. Both UTS and EB data show that there is a toughening effect of the IPN with increasing oxirane concentration. These results are the hallmark of synergism, and indirectly show proof of concept that a true IPN has developed, and that it strengthens the resin. Further research is required in order to better understand and optimize the system.

Figure 14:
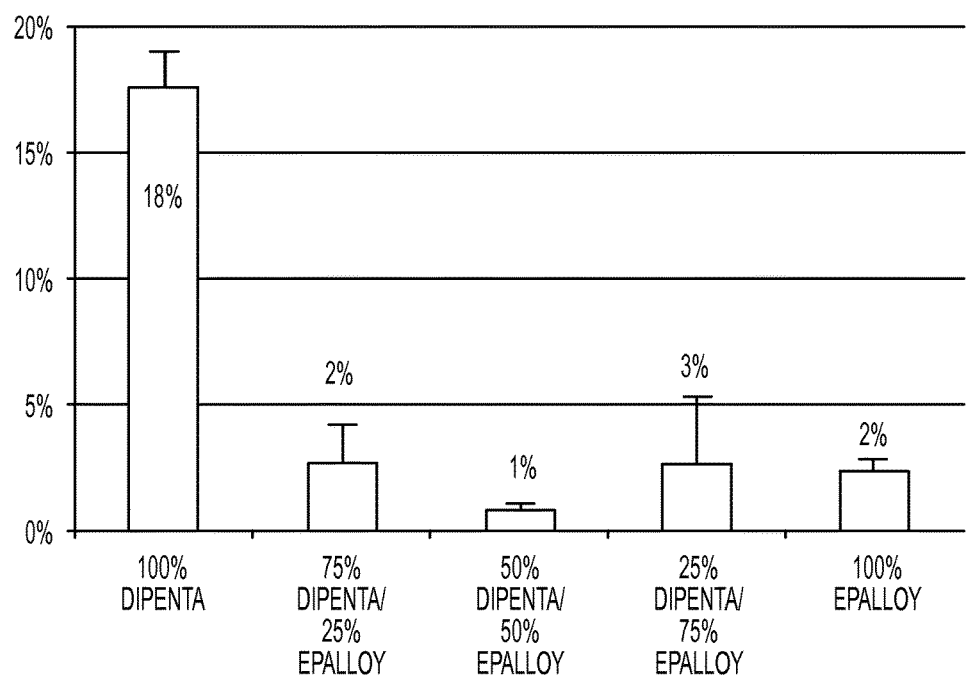
FIG. 14 shows water sorption results of resins in accordance with an embodiment of the invention.

Water sorption results (FIG. 14) show that 100% DIPENTA absorbed significantly more water than all other groups, and that the addition of oxirane significantly decreased water sorption. These results further support the utility of the hydrophobic oxirane monomers described in FIGS. 3 and 8.

Figure 15:
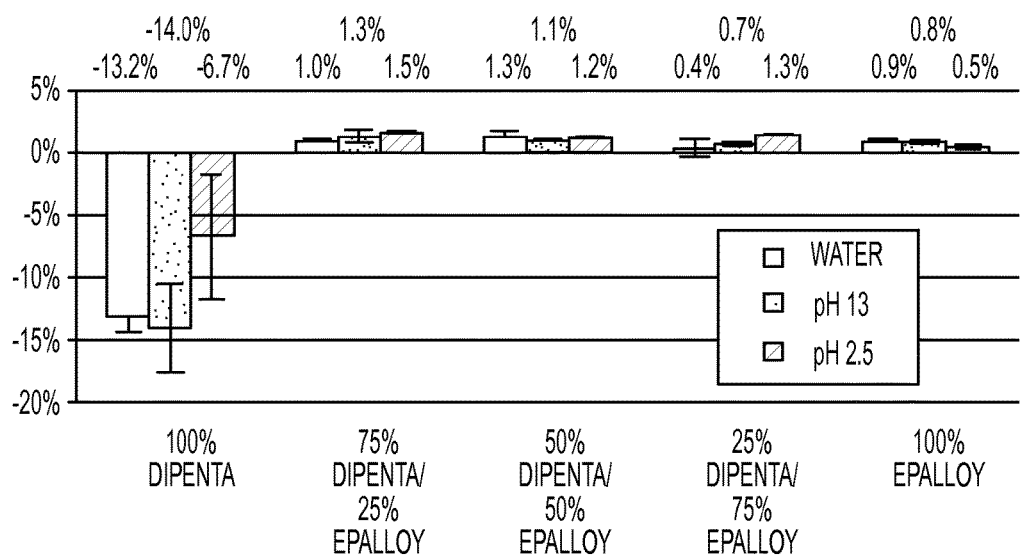
FIG. 15 shows degradation results of resins in accordance with an embodiment of the invention.

Degradation results (FIG. 15) show that not all the absorbed water was dried from the samples. Thus it is difficult to assess degradation in all groups except for 100% DIPENTA. There was significant hydrolysis (water group) and degradation in both acid and base groups. Interestingly there was significantly more degradation in the water group than the acid group.

Figure 1:
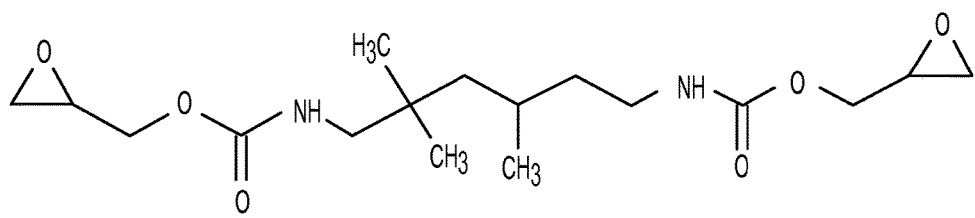
FIG. 1 shows the structure of urethane dioxirane monomer in accordance with an embodiment of the invention.
Figure 2:
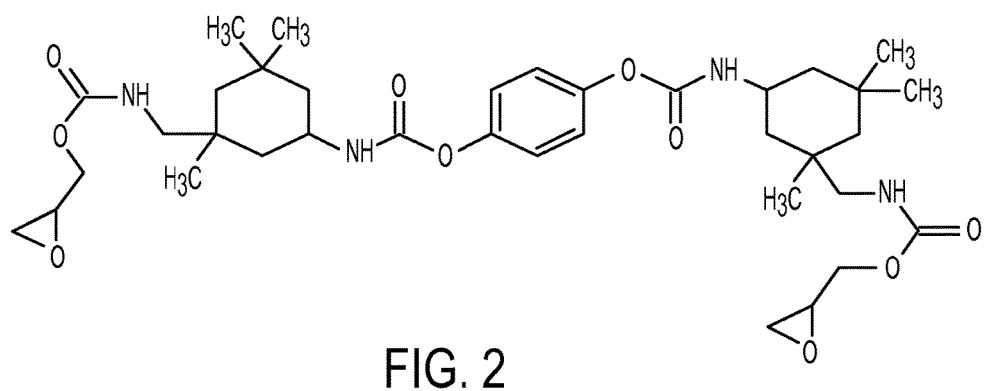
FIG. 2 shows the structure of diisophorone urethane dioxirane in accordance with an embodiment of the invention.
Figure 3:
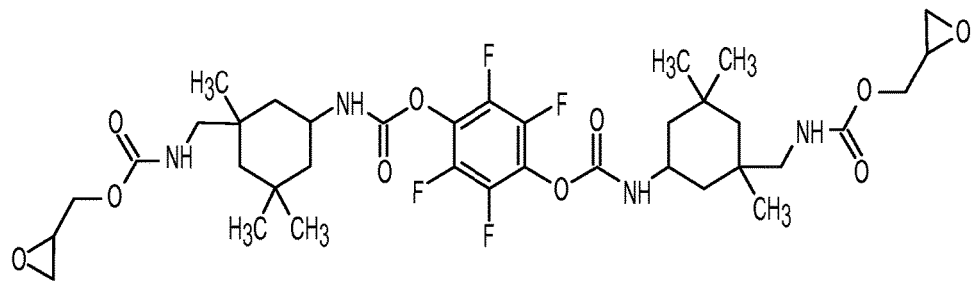
FIG. 3 shows the structure of tetrafluoro diisophorone urethane dioxirane in accordance with an embodiment of the invention.
Figure 4:
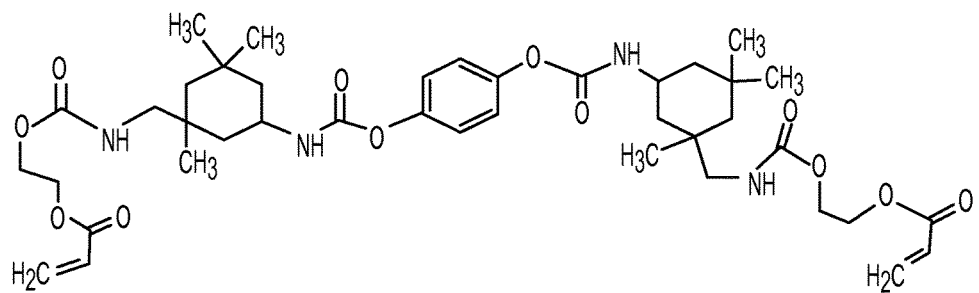
FIG. 4 shows the structure of diisophorone urethane diacrylate in accordance with an embodiment of the invention.
Figure 5:
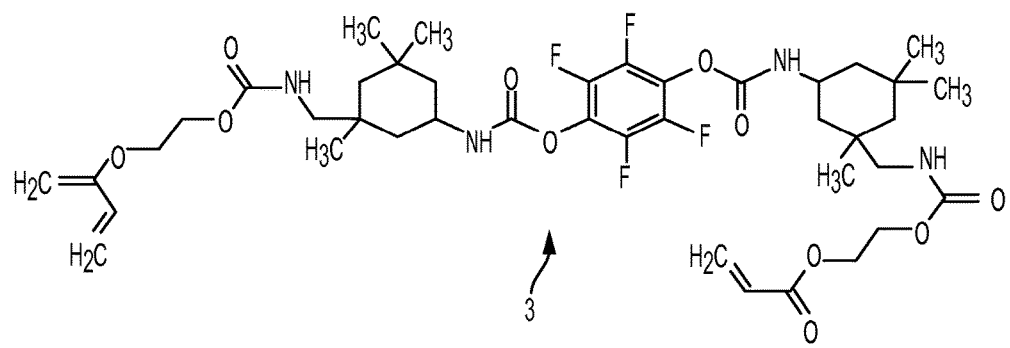
FIG. 5 shows the structure of tetrafluoro diisophorone urethane diacrylate in accordance with an embodiment of the invention.

In summary, these results demonstrate the concept that the OASys approach decreases susceptibility to oxygen inhibition, increase degree of cure, increase mechanical properties, and decrease water sorption and degradation in water, acid and base over either the acrylate or epoxide alone. These results demonstrate the great potential for the OASys to increase restorative clinical longevity. However, more hydrophobic monomers, as described in FIGS. 3 and 5, are needed to optimize and maximize these properties, and a tri-functional bonding agent is needed to translate this system to the clinic.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments will become apparent to those of ordinary skill in the art upon reading the foregoing description. Accordingly, this invention includes all modifications and equivalents of the subject matter recited in the claims appended hereto.

What is claimed is:

1. A dental composition comprising:
at least one cationically reactive compound;
at least one cationic photoinitiator;
at least one organic monomer comprising urethane dioxirane;
at least one compound comprising reactive acrylate monomers;
at least one free radical initiator;
at least one compound which is an organic monomer, the at least one compound comprising at least one of oxirane monomers, oxetane monomers, or alkenyl ether monomers; and
silver nanoparticles that help prevent caries.

2. The dental composition of claim 1, wherein the cationic photoinitiator is an iodonium salt.

3. The dental composition of claim 1, wherein the free radical initiator is an aromatic ketone or diketone.

4. The dental composition of claim 1,
wherein the at least one compound comprises oxirane monomers; and
further comprising an interpenetrating polymer network formed by the reactive acrylate monomers and the oxirane monomers.

5. The dental composition of claim 1, wherein the composition further comprises acrylate monomers in an interpenetrating polymer network with acrylate/oxirane hybrid monomers.

6. The dental composition of claim 4, wherein a ratio of the reactive acrylate monomers to the oxirane monomers is selected from the group consisting of 0:100, 25:75, 50:50, 75:25 and 100:0 wt %.

7. The dental composition of claim 5, wherein the acrylate monomer is a urethane acrylate.

8. The dental composition of claim 7, wherein the urethane acrylate is fluorinated.

9. The dental composition of claim 1, further comprising an amine curing agent.

10. The dental composition claim 9, wherein the amine curing agent is selected from diethylenetriamine (DTA), triethylenetetramine (TTA), N-aminoethylpiperazine (N-AEP), isophoronediamine (IPDA), metaphenylenediamine (MPDA), hexamethylene diamine (HMDA), and ethyl-4-dimethyl-aminobenzoate (EDMAB).

* * * * *